United States Patent [19]

Patton et al.

[11] Patent Number: 5,053,542
[45] Date of Patent: Oct. 1, 1991

[54] CATALYTIC BROMINATION OF 2-FLUOROANILINE

[75] Inventors: Jerry R. Patton; Narayanasamy Gurusamy, both of Baldwin, Mo.

[73] Assignee: Mallinckrodt Specialty Chemicals Company, St. Louis, Mo.

[21] Appl. No.: 472,930

[22] Filed: Jan. 31, 1990

[51] Int. Cl.$^5$ ............................................ C07C 209/74
[52] U.S. Cl. .................................................... 564/412
[58] Field of Search .......................................... 564/412

[56] References Cited

U.S. PATENT DOCUMENTS 3,987,057 10/1976 Goddard ...................... 260/326 HL
4,138,242 2/1979 Goddard ................................. 71/92
4,443,631 4/1984 Padilla ................................. 564/412

Primary Examiner—Richard L. Raymond
Attorney, Agent, or Firm—Rothwell, Figg, Ernst & Kurz

[57] ABSTRACT

A process for the production of 2,4-dihaloaniline, especially 4-bromo-2-fluoroaniline, via the halogenation (bromination) of 2-haloaniline (2-fluoroaniline) in the presence of quaternary ammonium halide (bromide) catalyst in an inert solvent. The yield and selectivity are very high and the inventive method includes continuous processing with recycle of the catalyst/solvent mixture.

16 Claims, No Drawings

CATALYTIC BROMINATION OF 2-FLUOROANILINE

FIELD OF THE INVENTION

The present invention broadly relates to the halogenation of 2-haloaniline to produce a 2,4-dihaloaniline. More specifically, the invention relates to a process for the production of 4-bromo-2-fluoroaniline from 2-fluoroaniline and molecular bromine in the presence of a quaternary ammonium bromide catalyst.

BACKGROUND OF THE INVENTION 2,4-dihaloanilines in general, and 4-bromo-2-fluoroaniline in particular, are useful, inter alia, in the preparation of pharmaceutical and agricultural chemicals. The preparation of these useful chemical intermediates, until now, has been cumbersome and expensive. Prior art processes for the production of 4-bromo-2-fluoroaniline, for example, may require the use of expensive and/or difficult-to-obtain brominating agents.

One process for the preparation of 4-bromo-2-fluoroaniline (and its use in the preparation of arylpropionic acids) is taught in U.S. Pat. No. 4,443,631 to Padilla, issued Apr. 17, 1984. 1,3-dibromo-5,5-dimethylhydantoin in dimethylformamide (DMF) is prepared under nitrogen and is added to a solution of 2-fluoroaniline in DMF maintained at −34° to −23° C. with a dry ice-acetone bath. Other brominating agents reportedly useful are N-bromoamides or -imides such as N-bromoacetamide or N-bromosuccinimide.

U.S. Pat. No. 3,987,057 (Goddard, Oct. 19, 1976) references the production of 4-bromo-2-fluoroaniline from 2-fluoroaniline and N-bromo-succinimide.

U.S. Pat. No. 4,138,242 (Goddard, Feb. 6, 1979) relates to herbicidal compounds and their preparation from 4-chloro-2-fluoroaniline. The 4-chloro-2-fluoroaniline is prepared through the chlorination of 2-fluoroacetanilide to yield 4-chloro-2-fluoroacetanilide and the subsequent formation of the desired aniline.

It is an object of the present invention to provide a simple, safe and relatively inexpensive process for the production of 2,4-dihalo-anilines.

SUMMARY OF THE INVENTION

In accordance with one aspect of the invention, 2,4-dihaloaniline is prepared by halogenating a 2-haloaniline with a halogenating agent in the presence of a quaternary ammonium halide catalyst and then neutralizing the resulting 2,4-dihaloaniline hydrohalide salt.

Preferably, the 2,4-dihaloaniline is prepared via a continuous process wherein a 2-haloaniline is added to a mixture of a molecular halogen and quaternary ammonium halide catalyst in an inert solvent. The desired dihalo-aniline precipitates as its hydrohalide salt which is readily recovered and then neutralized to yield the desired free compound. In the event the hydrohalide salt is to be used in a subsequent reaction, neutralization is omitted. The process consumes essentially all of the molecular halogen, and the remaining quaternary ammonium halide in the solvent preferably is recycled for further use. Operation of the present process in the batch mode also is possible.

DETAILED DESCRIPTION OF THE INVENTION

The process of the present invention can be used to produce various 2,4-dihaloanilines. In a preferred embodiment, the 2,4-dihaloaniline produced is 2-bromo-4-fluoroaniline.

In accordance with the process of the invention, a 2-haloaniline is halogenated with a halogenating agent in the presence of a quaternary ammonium halide, and the resulting 2,4-dihaloaniline hydrohalide salt is neutralized. According to one embodiment, a mixture of a molecular halogen and a quaternary ammonium halide is prepared in an inert solvent. The molecular halogen can be selected from molecular bromine, and chlorine, and the quaternary ammonium halide is selected such that the halide thereof corresponds with the molecular halogen chosen (quaternary ammonium bromide and molecular bromine, for example). The molecular halogen and the quaternary ammonium halide are mixed in the inert solvent in a molecular (molar) ratio that ranges from about 1:1 to 1.05:1. Preferably, the ratio is about 1:1.

The inert solvent selected can be chosen from a variety of known inert solvents. Aprotic solvents generally are useful so long as the reactants are soluble therein and the halogenated salt product is not. Hexane, heptane, carbon tetrachloride and chloroform are suitable solvents for use in the process. A preferred solvent for the process of this invention is dry methylene chloride. The solvent preferably is employed in relative excess of the reactants in order to facilitate separation of the desired end product and handling of the reaction by-products.

The solvent containing the molecular halogen and halide salt is stirred at room temperature. The 2-haloaniline to be halogenated is added to the mixture at ambient temperature while stirring, usually resulting in an immediate slight exotherm. The ratio of 2-haloaniline to molecular halogen desirably ranges from about 0.8:1 to 1:1, with the 1:1 ratio being preferred. The reaction goes to completion virtually immediately.

The temperature of the mixture containing the desired reaction product is lowered (for example to about 20° C.) by conventional means, for example a cooling jacket or cooling loop, whereupon the hydrohalide salt of the 2,4-dihaloaniline (e.g., hydrobromide salt of 4-bromo-2-fluoroaniline) precipitates. The precipitated salt is easily removed from the solution via centrifugation and/or filtration. The salt is suspended in methylene chloride, neutralized at basic pH (preferably between pH 7 and 8), and the layers are separated. The solvent layer can be evaporated (for example by rotovapor) to leave the oily product. Yields seen in a continuous-mode version of the process are approximately 95 percent, and are even higher in batch mode.

The solvent-catalyst solution remaining after removal of the precipitated hydrohalide salt is conveniently recycled for further use by the subsequent addition of halogen and 2-haloaniline. This recycling further increases yields.

The usefulness and advantages of the present invention are reflected in its high yield and high specificity to the desired 2,4-dihaloaniline.

The following examples are provided for illustrative purposes and are not to be construed as limiting.

EXAMPLE 1

33.5 g (0.104 mol) of tetrabutylammonium bromide were slowly added over 5 minutes to 100 ml of dry methylene chloride at ambient temperature in a glass vessel with stirring. 16.5 g (0.103 mol) of molecular bromine in 10 ml dry methylene chloride were added with stirring. The temperature rose from 20° C. to 38° C. After 10 minutes 11.33 g (0.103 mol) of 2-fluoroaniline were added in one portion. The temperature quickly rose from 20° C. to 40° C. The vessel was placed in an ice bath, and the temperature quickly returned to ambient. A precipitate formed on cooling. The precipitate was filtered, washed with fresh, dry methylene chloride and weighed. 8.6 g were recovered.

The reaction medium was reused in a second reaction. 16.5 g (0.103 mol) of molecular bromine were added along with 4.9 g tetrabutylammonium bromide to replace catalyst lost in transfers. The procedure was repeated with 11.3 g (0.103 mol) of 2-fluoroaniline. The total recovery from both reactions was 27.1 g 4-bromo-2-fluoroaniline hydrobromide, a 97% yield.

EXAMPLE 2

The procedure of Example 1 was repeated using catalyst in molar excess over molecular bromine, which was in molar excess over the 2-fluoroaniline. The quantities used were 45.1 g (0.14 mol) tetrabutylammonium bromide
19.2 g (0.12 mol) molecular bromine
10.9 g (0.10 mol) 2-fluoroaniline 130 ml dry methylene chloride were used. A trace of dibrominated fluoroaniline was detected in the recovered product by LC analysis.

EXAMPLE 3

Preparation of 4-Bromo-2-Fluoroaniline by Iterative Process

Cycle 1. Methylene chloride, 125 ml, and 32.2 g (0.1 mol) tetrabutylammonium bromide were mixed in a 200-ml, 3-necked roundbottom flask, equipped with a mechanical stirrer, a thermometer, an addition funnel and a water condenser leading to a mineral oil bubbler. Bromine, 16.0 g (0.1 mol), was added to the mixture over 15 minutes at room temperature. The temperature of the mixture rose from 24° C. to 30° C. The contents of the flask were stirred for 30 minutes. 2-Fluoroaniline, 11.1 g (0.1 mol), at room temperature was added to the mixture in one portion. The temperature of the mixture rose to 40° C. The orange solution immediately turned yellowish. After stirring for 15 minutes, the solution turned milky and the temperature was 32° C. After 30 more minutes solids were observed. The solution was filtered and the solids washed with ice-cold methylene chloride until white. On air-drying 9 g of product (Solid I) was obtained. The melting point was >200° C. LC analysis showed only desired product with a trace of impurity. LC analysis of the mother liquor (I) showed that it contained some desired product and some dibrominated compound.

Cycle 2. The mother liquor I was placed in the same apparatus described for Cycle 1. Bromine, 16.0 g (0.1 mol), was added to it at room temperature. The reddish suspension was stirred for 10 minutes, and 11.1 g (0.1 mol) 2-fluoroaniline were added in one portion at room temperature. After 15 minutes the solution was a milky suspension. After stirring for an additional hour, the solids were filtered off, washed with ice-cold methylene chloride and air-dried to yield 20 g (Solid II). The mother liquor (II) was brownish in color and LC analysis showed it contained desired product, some unreacted 2-fluoroaniline and some dibrominated impurity.

Cycle 3. The mother liquor II was again mixed with bromine, 16.0 g (0.1 mol), and 2-fluoroaniline, 11.1 g (0.1 mol), was added as above. After stirring for 30 minutes the white solid was filtered off and washed. 12 g (Solid III) were obtained. The mother liquor (III) was analyzed and again contained product, 2-fluoroaniline and impurity.

Cycle 4. The mother liquor III was used to repeat the previous step. The reaction mixture was stirred for 2 hours after the 2-fluoroaniline was added and then allowed to stand at room temperature overnight. Solid IV, 28 g, was isolated as above.

Cycle 5. The mother liquor IV was used to repeat the previous steps. The reaction mixture was stirred for 3 hours after the 2-fluoroaniline was added. The white solids were isolated, yielding 28 g. The brownish mother liquor was analyzed by LC and found to contain some desired product with minor amounts of 2-fluoroaniline and dibrominated impurity.

Salt Neutralization. All solids from Cycle I to Cycle 5 were combined for a total of 97 g, 71% of theory. The salt was dissolved in 200 ml methylene chloride and the solution was stirred while adding dilute sodium hydroxide until it was neutral to litmus. The methylene chloride layer was separated, washed three times with 200 ml portions of water and evaporated in a rotovapor to yield 65 g of a light yellow oil. Fractional distillation produced the following:

| | |
|---|---|
| Precut | 6 g, analyzed as product and 2-fluoroaniline (added to mother liquor for subsequent workup); |
| Main Cut | 51 g, analyzed by capillary LC to be 99% pure 4-bromo-2-fluoroaniline and 0.776% dibrominated impurity; |
| Pot Residue | analyzed as product and a considerable amount of the dibrominated impurity (also added to mother liquor for workup). |

NMR analyses of the Main cut confirmed the structure to be the desired product.

Mother Liquor Workup. The mother liquor V was combined with the Precut and the Pot Residue from the salt neutralization step. The combined mixture was neutralized with dilute sodium hydroxide solution to neutral by litmus, washed twice with 200 ml portions of water, dried using a molecular sieve and evaporated in a rotovapor to yield 55 g of a brownish viscous oil. Fractional distillation under pump vacuum yielded a 30 g main cut that was 90% desired product by LC analysis.

The total isolated yield was 81 g, 85% of theory.

Although the invention has been described in connection with certain preferred embodiments and specific Examples, it is not so limited. Modifications with the scope of the claims will be readily apparent to those skilled in the art.

We claim:

1. A process for the production of 2,4-dihaloaniline comprising halogenating 2-haloaniline with a halogenating agent in the presence of a quaternary ammonium halide and neutralizing the resulting 2,4-dihaloaniline hydrohalide salt.

2. A process according to claim 1 wherein the halogenating agent is molecular halogen.

3. A process according to claim 2 wherein the halogen of the quaternary ammonium halide is the same as the halogen of the molecular halogen halogenating agent.

4. A process for the production of 4-halo-2-fluoroaniline comprising halogenating 2-fluoroaniline with a halogenating agent in the presence of a quaternary ammonium halide and neutralizing the resulting 4-halo-2-fluoroaniline hydrohalide salt.

5. A process according to claim 4 wherein said halogenating step is conducted in an inert solvent.

6. A process according to claim 5 wherein said inert solvent is methylene chloride.

7. A process according to claim 4 wherein said halogenating step comprises adding molecular halogen to 2-fluoroaniline and quaternary ammonium halide in an inert solvent.

8. A process of claim 7 wherein said inert solvent comprises methylene chloride.

9. A process of claim 4 wherein said neutralizing step comprises adding the 4-halo-2-fluoroaniline hydrohalide salt to an aqueous solution having a basic pH.

10. A process of claim 9 wherein said pH is between about 7 and 8.

11. A process for the preparation of 4-bromo-2-fluoroaniline, comprising:

(a) providing a mixture of bromine and quaternary ammonium bromide in an inert solvent;
(b) adding 2-fluoroaniline to said mixture; and
(c) precipitating 4-bromo-2-fluoroaniline as its hydrobromide salt.

12. A process of claim 11 wherein said mixture of step (a) comprises substantially equimolar amounts of bromine and quaternary ammonium bromide.

13. A process of claim 11 wherein said inert solvent comprises methylene chloride.

14. A process of claim 11 wherein said precipitating step (c) is conducted at about 20° C.

15. A process of claim 11 further comprising:
(d) neutralizing said hydrobromide salt to yield 4-bromo-2-fluoroaniline.

16. A continuous process for the production of 4-bromo-2-fluoroaniline comprising:
(a) adding 2-fluoroaniline to a mixture of bromine and quaternary ammonium bromide in an inert solvent to produce 4-bromo-2-fluoroaniline hydrobromide salt as a precipitate in a mother liquor;
(b) recovering said precipitate and recycling said mother liquor.

* * * * *

REEXAMINATION CERTIFICATE (2504th)
United States Patent [19]
Patton et al.

[11] B1 5,053,542
[45] Certificate Issued   Mar. 14, 1995

[54] CATALYTIC BROMINATION OF 2-FLUOROANILINE

[75] Inventors: Jerry R. Patton; Narayanasamy Gurusamy, both of Baldwin, Mo.

[73] Assignee: Mallinckrodt Specialty Chemicals Company, St. Louis, Mo.

Reexamination Request:
  No. 90/003,361, Mar. 18, 1994

Reexamination Certificate for:
  Patent No.: 5,053,542
  Issued:    Oct. 1, 1991
  Appl. No.: 472,930
  Filed:     Jan. 31, 1990

[51] Int. Cl.⁶ ............................................ C07C 209/74
[52] U.S. Cl. ..................................................... 564/412
[58] Field of Search ........................................ 564/412

[56] References Cited

U.S. PATENT DOCUMENTS 3,987,057  10/1976  Goddard ...................... 260/326 HL
4,138,242   2/1979  Goddard ................................ 71/92
4,443,631   4/1984  Padilla ................................ 564/412

OTHER PUBLICATIONS

The Chemistry of the Amino Group, Edited by Saul Patai, The Hebrew University, Jerusalem, Israel, 1968, Interscience Publishers.
Bromation régiosélective en série aromatique. I: Monobromation en position *para* de phénols et d'amines aromatiques par le tribromure de tétrabutylammonium, J. Berthelot et al, Can. J. Chem. 67, 2061 (1989).
Regioselective Bromination in the Aromatic Series. I: Monobromination in Para Position of Phenols and Aromatic Acids by Tetrabutylamonnium Tribromide, J. Berthelot et al, Can. J. Chem. 67, 2061 (1989).
Regioselective Monobromination of Aromatic Amines with Tetrabutylammonium Tribromide, J. Berthelot et al., Synth. Commun., 16, 1641 (1986).
Halogenation Using Quaternary Ammonium Polyhalides. VI. Bromination of Aromatic Amines by Use of Benzyltrimethylammonium Tribromide, Shoji Kajigaeshi et al, Feb. 1988, The Chemical Society of Japan.
Selective Bromination of Aromatic Amines by Use of Tetrbutylammonium Tribromide and Benzyltrimethylammonium Tribromide, Takaaki Kainami et al., Res. Rep. of Ube Tech. Coll., No. 35 Mar., 1989.
Selected Experiments in Organic Chemistry, Second Edition, George K. Helmkamp and Harry W. Johnson, Jr., University of California, Riverside, 1968.
Advanced Organic Chemistry, Reactions, Mechanisms, and Structure, Second Edition, Jerry March, Adelphi University, 1977.

*Primary Examiner*—Richard L. Raymond

[57] ABSTRACT

A process for the production of 2,4-dihaloaniline, especially 4-bromo-2-fluoroaniline, via the halogenation (bromination) of 2-haloaniline (2-fluoroaniline) in the presence of quaternary ammonium halide (bromide) catalyst in an inert solvent. The yield and selectivity are very high and the inventive method includes continuous processing with recycle of the catalyst/solvent mixture.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-16 is confirmed.

* * * * *